United States Patent [19]

Maruyama

[11] Patent Number: 5,679,874
[45] Date of Patent: Oct. 21, 1997

[54] PROCESS FOR THE PREPARATION OF DICHLORO-(2,2)-PARACYCLOPHANE

[75] Inventor: Hiroshi Maruyama, Chiba-ken, Japan

[73] Assignee: Daisan Kasei Kabushiki Kaisha, Tokyo, Japan

[21] Appl. No.: 913,742

[22] Filed: Jul. 14, 1992

Related U.S. Application Data

[63] Continuation of Ser. No. 636,081, Dec. 28, 1990, abandoned.

[30] Foreign Application Priority Data

Dec. 29, 1989 [JP] Japan ................................. 1-342230
Apr. 19, 1990 [JP] Japan ................................. 2-101715

[51] Int. Cl.$^6$ ........................... C07C 21/18; C07C 211/00
[52] U.S. Cl. ........................ 570/149; 570/184; 570/210; 564/282; 564/289
[58] Field of Search ............................. 570/210, 184, 570/149; 564/282, 289

[56] References Cited

U.S. PATENT DOCUMENTS

| | | | |
|---|---|---|---|
| 4,783,561 | 11/1988 | Pregagha et al. | 570/184 |
| 4,816,608 | 3/1989 | Bornengo et al. | 570/184 |
| 4,831,199 | 5/1989 | Suzuki et al. | 570/207 |
| 4,849,559 | 7/1989 | Lee et al. | 570/184 |
| 4,853,488 | 8/1989 | Ungarelli et al. | 570/184 |

OTHER PUBLICATIONS

Fieser et al Reagents for Organic Synthesis pp. 1109–1110 (1967).

*Primary Examiner*—Alan Siegel
*Attorney, Agent, or Firm*—McAulay Fisher Nissen Goldberg & Kiel, LLP

[57] ABSTRACT

Process for the preparation of dichloro-(2,2)-paracyclophane from p-methylbenzylhalide through 2(3)-chloro-p-methylbenzyltrimethylammonium halide by Hofmann elimination of 2(3)-chloro-p-methylbenzyl trimethylammonium hydroxide in an aqueous solution of alkali metal hydroxide, wherein the 2(3)-chloro-p-methylbenzyltrimethylammonium halide is prepared by chlorination of p-methylbenzyltrimethylammonium halide and the Hofmann elimination is conducted in the presence of dioxane.

11 Claims, No Drawings

PROCESS FOR THE PREPARATION OF DICHLORO-(2,2)-PARACYCLOPHANE

This is a continuation of application Ser. No. 07/636,081, filed Dec. 28, 1990, now abandoned.

BACKGROUND OF THE INVENTION

1. Field of the Invention

This invention relates to a process for the preparation of dichloro-(2,2)-paracyclophane having the following general formula:

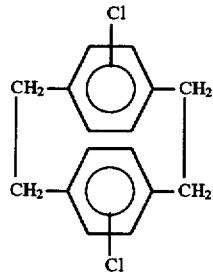

The compound is well known in literature and is generally utilized as an intermediate in the preparation of the corresponding monochlorinated poly-p-xylylene, which is usefully employed in the preparation of coating films having highly improved electronic and high temperature characteristics by vacuum vapor deposition technique in the field of electronic devices and space industries devices.

2. Prior Art

In the past, direct chlorination of (2,2)-paracyclophane was employed for the preparation of dichloro-(2,2)-paracyclophane, which was accompanied by contamination with a trace of impurities imparting undesirable properties to the final polymer film.

Thus, recent attention is paid to the following process:

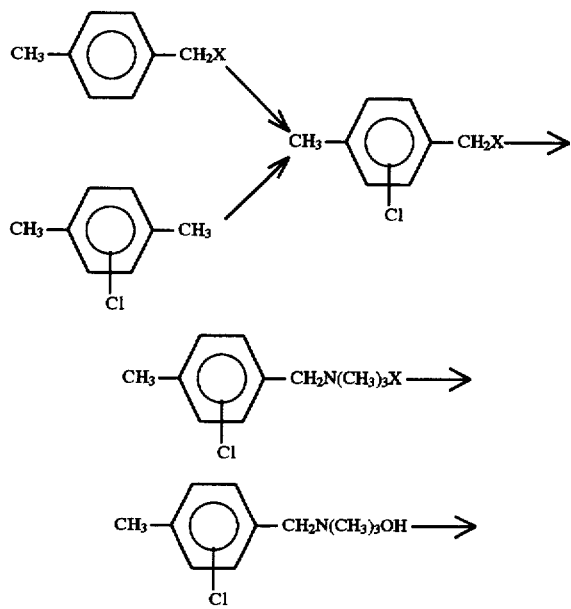

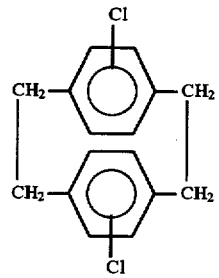

wherein X is a halogen such as chlorine or bromine.

According to the process, 2 or 3 (hereinafter referred to as 2(3))-chloro-p-methylbenzylhalide is prepared by chlorination of monochloro-p-xylene or by chlorination of p-methylbenzylhalide. Then it is reacted with trimethylamine to obtain 2(3)-chloro-p-methylbenzyltrimethylammonium halide (hereinafter referred to as chlorinated quaternary ammonium salt). The chlorinated quaternary ammonium salt is reacted with an alkali metal hydroxide to obtain 2(3)-chloro-p-methylbenzyltrimethylammonium hydroxide, (hereinafter referred to as chlorinated quaternary ammonium hydroxide) which is then subjected to Hofmann elimination to lead to dichloro-(2,2)-paracyclophane.

However, in the process, there are two problems to be solved for commercial production. One of them is in the chlorination or the halogenation method. As is known, 2(3)-chloro-p-methylbenzylhalide is prepared through two different courses. In either course, it is not so easy to obtain only desired monochloro derivatives with excellent yields. The chlorination or the halogenation provides not only desired derivatives, 2(3)-chloro-p-methylbenzylhalide, but also undesired byproducts having two or more halogen atoms on the benzene ring and those having halogen atoms on methyl radicals, giving only low yields and needing further complicated refining process for isolating the desired derivatives.

Another problem is in difficulty for obtaining considerable yields in Hofmann elimination. It was reported that some solvents like dimethylsulfoxide (U.S. Pat. No. 4,532,369), mono- or poly-ethyleneglycoldialkylether (European Patent No.0253,191), etc. can improve the yields in Hofmann elimination. However, those solvents are not so desirable in view of their toxicity or expensiveness.

Accordingly, an object of the present invention is to provide a novel and easy method for monochlorination on benzene ring in the process for the preparation of chlorinated quaternary ammonium salt.

Another object of the invention is to provide a novel solvent for Hofmann elimination in the preparation of dichloro-(2,2)-paracyclophane.

SUMMARY OF THE INVENTION

According to the present invention, there is provided a process for the preparation of dichloro-(2,2)-paracyclophane from p-methylbenzylhalide through chlorinated quaternary ammonium salt by Hofmann elimination of chlorinated quaternary ammonium hydroxide in an aqueous solution of an alkali metal hydroxide, wherein the chlorinated quaternary ammonium salt is prepared by chlorination of p-methylbenzyltrimethylammonium halide (herein after referred to as quaternary ammonium salt) and the Hofmann elimination is carried out in the presence of dioxane.

The reaction sequence of the invention can be shown as follows:

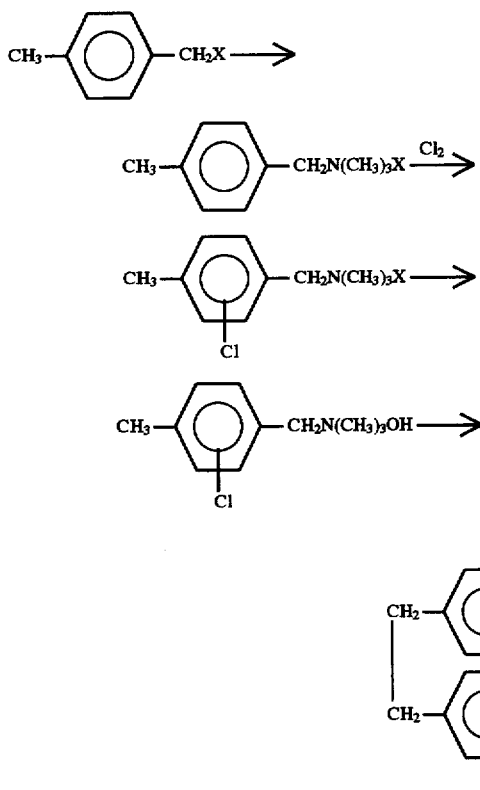

wherein X is a halogen such as chlorine or bromine.

As explained above, a useful method for monochlorination of benzene ring in the process of the preparation of chlorinated quaternary ammonium salt is provided, together with a novel solvent for Hofmann elimination of chlorinated quaternary ammonium hydroxide in the preparation of dichloro-(2,2)-paracyclophane.

The inventor has found unexpectedly that desired derivatives having one chlorine atom on a benzene ring can be obtained easily and selectively by chlorination of quaternary ammonium salt, which is prepared by reacting p-methylbenzylhalide with an aqueous solution of trimethylamine as seen from the following:

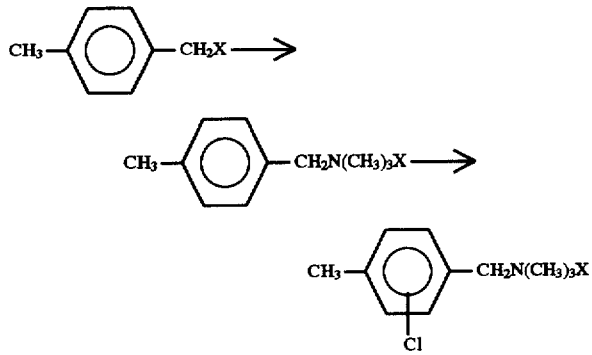

wherein X is a halogen such as chlorine or bromine.

Thus, chlorination can be greatly simplified with excellent yields and needing no further refining process.

In the present invention, the chlorination is conducted by feeding chlorine gas into an aqueous solution of the quaternary ammonium salt. The aqueous solution heated through exothermic reaction is cooled to keep a moderate temperature range between 0° C. and 60° C. Higher temperature than 60° C. causes side reaction resulting in low product yields and lower temperature than 0° C. often results in precipitation of the quaternary ammonium salt, thereby disturbing sufficient mixing for reaction. Termination of the reaction can be detected by gaschromatographic analysis through the following reaction under elevated temperature:

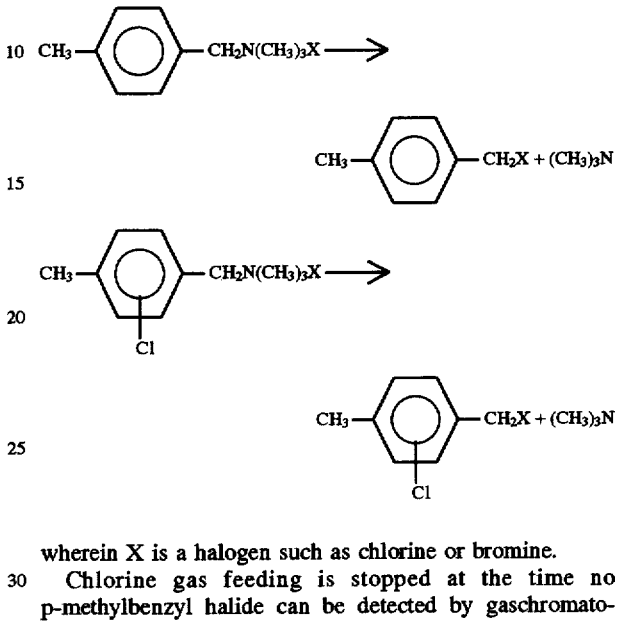

wherein X is a halogen such as chlorine or bromine.

Chlorine gas feeding is stopped at the time no p-methylbenzyl halide can be detected by gaschromatographic analysis of the reaction solution. Excess chlorine in the solution is to be expelled by passing an inert gas such as nitrogen through the solution. An aqueous solution of the chlorinated quaternary ammonium salt thus obtained, which is an intermediate in the preparation of dichloro-(2,2)-paracyclophane, is then subjected to successive reaction. Dichloro-(2,2)-paracyclophane can be prepared with improved yields by conducting Hofmann reaction of the chlorinated quaternary ammonium hydroxide prepared in situ by the action of alkali metal hydroxide on the chlorinated quaternary ammonium salt, in the presence of dioxane. Dioxane is a more inexpensive solvent or less toxic solvent than conventional solvents for Hofmann elimination. The amount of dioxane to be added to the reaction medium may vary in a wide range. Ratios of the volume (ml) of dioxane to the weight (g) of p-methylbenzyl halide are advantageously between 5° and 30°. The Hofmann elimination is conducted in an alkaline medium containing alkali metal hydroxide. The mole ratios of the alkali metal hydroxide to the p-methylbenzylhalide are preferably between 2 and 8, covering the alkaline amount used for the formation of chlorinated quaternary ammonium hydroxide from the chlorinated quaternary ammonium salt. The alkali metal hydroxide includes sodium hydroxide and potassium hydroxide and potassium hydroxide is preferably used. Hofmann elimination can be conducted in a wide range of concentration of an aqueous solution of alkali metal hydroxide in the reaction medium, preferably in 40% or more concentration. The concentration of alkali metal hydroxide is characteristic in the present invention, compared with a known process (European patent No. 0,220,744) wherein the concentration of alkalimetal hydroxide lower than 40% is essential for the process. According to the present invention, Hofmann elimination is carried out preferably at a temperature between 60° C. and 90° C. The reaction time depends naturally on the reaction temperature. For example, the sufficient time for completing the reaction is about 4 hours at 80° C. Before Hofmann elimination, addition of some reductants like sodium borohydride is preferable for obtaining a more colorless product. After completing the reaction, the solution is diluted with water and precipitates from the solution are filtered and dried. Then, they are dissolved in toluene and filtered to remove insolubles and the toluene is distilled off, thus obtaining dichloro-(2,2)-paracyclophane.

DESCRIPTION OF PREFERRED EMBODIMENTS

The following examples are presented for better understanding of the present invention to those skilled in the art. It is also to be understood that these examples are intended to be illustrative only and are not intended to limit the invention in any ways.

EXAMPLE 1

14.0 g of p-methylbenzylchloride were reacted with 21.0 g of trimethylamine 30% aq. solution Under stirring. In the reaction, the solution was brought to 44° C. and then cooled. p-Methylbenzylchloride was completely dissolved in 1 hour with stirring, obtaining an aq. solution of quaternary ammonium salt. Chlorine gas was fed into the aq. solution of quaternary ammonium salt under stirring, while cooling the solution not to exceed 40° C. Reaction process was observed by gaschromatographic analysis. p-Methylbenzylchloride could not be detected by the chromatographic analysis after about 2 hours, then excess chlorine was expelled by feeding nitrogen for 30 minutes, thus obtaining an aq. solution of quaternary ammonium salt. 30 ml of dioxane were added thereto, followed by adding gradually 85% KOH under stirring and cooling, and neutralizing hydrogen chloride generated by the chlorination and dissolved into the solution. 10 g of KOH were added gradually to the solution changing pH of the solution into alkaline. 30 g of further 85% KOH were added thereto. The solution was heated to 80° C. in about 1 hour and a half and it was maintained at the temperature for further 4 hours. Then the solution was cooled and diluted with water. Precipitates occured were filtered and dried, giving 12.5 g of crude dichloro-(2,2)-paracyclophane (yield 90.6%). The crude product was dissolved in 70 ml of toluene under heating and filtered to remove insolubles and then the toluene was distilled off, thus obtaining dichloro-(2,2)-paracyclophane. The purity determined by gaschromatographic analysis was more than 95%. Thus, 12.4 g of dichloro-(2,2)-paracyclophane were obtained (yield 89.9%).

EXAMPLE 2

Example 1 was repeated excepting that 30 g of 85% KOH in total instead of 40 g of 85% KOH were added. 12.8 g of crude product (yield 92.8%) and 11.1 g of product (yield 80.4%) were obtained.

EXAMPLE 3

Example 1 was repeated excepting that 200 ml of dioxane instead of 300 ml dioxane were added. 13.2 g of crude product (yield 95.7%) and 11.4 g of product (yield 82.6%) were obtained.

EXAMPLE 4

Example 3 was repeated excepting that 200 ml of dioxane and 30 g of 85% KOH in total instead of 300 ml dioxane and 40 g of 85% KOH were added. 13.2 g of crude product (yield 95.7) and 10.5 g of product (yield 76.1%) were obtained.

EXAMPLE 5

14.0 g of p-methylbenzylchloride were reacted with 24.0 g of trimethylamine (30% aq. solution) while cooling with water. After obtaining a homogeneous solution, chlorine gas was fed into the solution, while maintaining the solution at a temperature of not more than 20° C. After completing the reaction, nitrogen gas was fed into the solution to expel excess chlorine. Then 160 ml of dioxane were added thereto. Also 38 g of 85% KOH dissolved in 34 ml of water were dropped with stirring, while cooling the solution at a temperature of not more than 40° C. Further, 2 ml of sodium borohydride solution (an aq. solution containing 12% sodium borohydride and 40% NaOH) were added thereto. The solution was brought to 80° C. in two and a half hours and it was maintained at the temperature for 40 hours. Then the reaction solution was treated in the same way as in Example 1. Thus, 12.3 g of crude product (yield 89.1%) were obtained, giving 10.2 g of product (yield 73.2%).

EXAMPLE 6

14.0 g of p-methylbenzylchloride were reacted with 48.0 g of trimethylamine 15% aq. solution with stirring. After obtaining a homogeneous solution, chlorine gas was fed into the solution, while maintaining the solution temperature at less than 5° C. During reaction precipitates occured to disturb mixing, thus 10 ml of water were added. Nitrogen gas was fed into the solution to expel excess chlorine after completing the reaction. Then 160 ml of dioxane were added thereto. 38 g of 85% KOH and 2 ml of sodium borohydride solution were added with stirring, maintaining the solution temperature at less than 20° C. The solution was brought to 80° C. in about 3 hours and maintained at the temperature for 40 hours. Then the solution was treated in the same way as in Example 1. Thus, 11.9 g of crude product (yield 86.2%) and 9.8 g of product (yield 71.0%) were obtained.

EXAMPLE 7

Example 5 was repeated excepting that chlorination was conducted at a temperature of not more than 50° C. and 11.6 g of crude product (yield 84.1%) and 10.3 g of product (yield 74.6%) were obtained.

What is claimed is:

1. A method for the preparation of 2(3)-chloro-p-methylbenzyltrimethylammonium halide comprising chlorinating p-methylbenzyltrimethylammonium halide.

2. The method of claim 1 wherein the chlorination is carried out with chlorine gas.

3. A method for the preparation of dichloro-(2,2)-paracyclophane comprising the steps of
    (a) chlorinating p-methylbenzyltrimethylammonium halide to obtain 2(3)-chloro-p-methylbenzyltrimethylammonium halide;
    (b) subjecting the 2(3)-chloro-p-methylbenzyltrimethylammonium halide to Hofmann elimination to produce dichloro-(2,2)-paracyclophane.

4. The method of claim 3 wherein the p-methyltrimethylammonium halide is prepared by reacting a p-methylbenzyl halide with an aqueous solution of trimethylamine.

5. The method of claim 3 wherein the chlorination is carried out with chlorine gas.

6. The method of claim 3 wherein the Hofmann elimination is carried out by reacting the 2(3)-chloro-p-methylbenzyltrimethylammonium halide in an aqueous solution with an alkali metal hydroxide and in the presence of dioxane.

7. A method for the preparation of 2(3)-chloro-p-methylbenzyltrimethylammonium halide comprising chlorinating p-methylbenzyltrimethylammonium halide in water solution with chlorine gas.

8. The method of claim 7 wherein the p-methylbenzyltrimethylammonium halide is prepared by reacting p-methylbenzyl halide with an aqueous solution of trimethylamine.

9. A method for the preparation of dichloro-(2,2)-paracyclophane comprising the steps of
   (a) chlorinating p-methylbenzyltrimethylammonium halide in water solution with chlorine gas to obtain 2(3)-chloro-p-methylbenzyltrimethylammonium halide;
   (b) subjecting the thus obtained 2(3)-chloro-p-methylbenzyltrimethylammonium halide to Hofmann elimination to obtain dichloro-(2,2)-paracyclophane.

10. The method of claim 9 wherein the p-methylbenzyltrimethylammonium halide is prepared by reaction p-methylbenzyl halide with an aqueous solution of trimethylamine.

11. The method of claim 9 wherein the Hofmann elimination is carried out by reacting an aqueous solution of the 2(3)-chloro-p-methylbenzyltrimethylammonium halide with an alkali metal hydroxide in the presence of dioxane.

* * * * *